(12) United States Patent
Schwartz et al.

(10) Patent No.: US 10,149,659 B1
(45) Date of Patent: Dec. 11, 2018

(54) HAND-HELD X-RAY SENSOR WITH GESTURE-ACTIVATED WAKE FUNCTION

(71) Applicant: VAREX IMAGING CORPORATION, Salt Lake City, UT (US)

(72) Inventors: Rudiger Schwartz, Sunnyvale, CA (US); Maxwell Allen, Redwood City, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 0 days.

(21) Appl. No.: 15/719,568

(22) Filed: Sep. 29, 2017

(51) Int. Cl.
  *A61B 6/00* (2006.01)
  *G03B 42/00* (2006.01)

(52) U.S. Cl.
  CPC .............. *A61B 6/56* (2013.01); *G03B 42/00* (2013.01)

(58) Field of Classification Search
  None
  See application file for complete search history.

(56) References Cited

U.S. PATENT DOCUMENTS

| 7,864,163 B2 | 1/2011 | Ording et al. | |
| 2006/0261296 A1* | 11/2006 | Heath | G03B 42/02 250/580 |
| 2013/0136235 A1* | 5/2013 | Liu | A61B 6/4233 378/98 |
| 2014/0380187 A1* | 12/2014 | Gardenfors | G06F 3/017 715/748 |
| 2018/0070909 A1* | 3/2018 | Kravis | G03B 42/042 |

* cited by examiner

*Primary Examiner* — Yara B Green
(74) *Attorney, Agent, or Firm* — Su IP Consulting

(57) ABSTRACT

An X-ray sensing apparatus includes a detector array configured to generate a plurality of signals in response to x-rays incident on the detector array during an exposure period; a high-clock logic device communicatively coupled to the detector array; a low-clock logic device communicatively coupled to the high-clock logic device; an accelerometer communicatively coupled to the low-clock logic device; and a processor communicatively coupled to the high-clock logic device. The low-clock logic device is configured to receive an acceleration signal from the accelerometer; determine that the acceleration signal corresponds to a wake gesture; and, in response to determining that the acceleration signal corresponds to the wake gesture, send a first power state change signal to the processor and a second power state change signal to the high-clock logic device.

20 Claims, 6 Drawing Sheets

HAND-HELD X-RAY SENSOR WITH GESTURE-ACTIVATED WAKE FUNCTION

BACKGROUND

Unless otherwise indicated herein, the approaches described in this section are not prior art to the claims in this application and are not admitted to be prior art by inclusion in this section.

Digital radiography is a form of X-ray imaging in which digital X-ray sensors are used to generate digital X-ray images, and has multiple advantages over traditional film-based techniques. By bypassing chemical processing, digital radiography is more time efficient, provides digital images for immediate image preview, facilitates image enhancement, and generally requires less radiation to produce an image of similar contrast.

Digital radiography is now used in many applications, including medical diagnostics, veterinary care, dental imaging, industrial inspection, and security. Each of these applications could benefit from a completely portable implementation of a flat panel X-ray acquisition system, i.e., a battery-powered device with full image acquisition, enhancement, and data storage capabilities. Consequently, flat panel display X-ray sensors have been developed with a form factor that can be easily carried and employed as a self-contained, battery powered device. However, the power requirements of such hand-held X-ray sensors can severely limit how long they can be operated without being charged, limiting the utility of the hand-held configuration.

To address this issue, some hand-held X-ray sensors are configured with a sleep function that causes the X-ray sensor to enter a lower power state after a certain time interval has elapsed in which the X-ray sensor remains idle. Thus, when the X-ray sensor is not in use, power consumption of the X-ray sensor is greatly reduced. An important drawback to such a sleep function is that waking the X-ray sensor can be time-consuming and inconvenient. For example, in veterinary applications, the X-ray sensor is typically not in use while an animal to be X-rayed is made ready for imaging, the X-ray sensor is correctly positioned near the animal, and an image acquisition computer external to the X-ray sensor is set up for receiving image data. As a result, there are extended periods of time during which the X-ray sensor can remain in a lower power consumption state, such as an idle state or a sleep state, without impacting the user. Unfortunately, waking the X-ray sensor from such a state can involve a user interrupting a current task (e.g., minding the animal, positioning the X-ray sensor, or positioning the X-ray generator), walking to the image acquisition computer, paging through one or more menus on the image acquisition computer and performing one or more input operations, and returning to the interrupted task. Thus, while the sleep function can extend battery life of a hand-held X-ray sensor, the added inconvenience of such a feature can overshadow its benefits.

SUMMARY

In accordance with at least some embodiments of the present disclosure, a computer-implemented method for changing a power state in a hand-held X-ray sensing apparatus that includes a processor, an accelerometer, a high-clock logic device, a low-clock logic device, and a detector array, includes receiving an acceleration signal from the accelerometer, determining with the low-clock logic device that the acceleration signal corresponds to a wake gesture, and, in response to the determining, sending, from the low-clock logic device, a first power state change signal to the processor and a second power state change signal to the high-clock logic device, and causing the detector array to exit a stand-by state and enter a ready state in which image acquisition can be performed.

In accordance with at least some embodiments of the present disclosure, an X-ray sensing apparatus includes a detector array configured to generate a plurality of signals in response to x-rays incident on the detector array during an exposure period, a high-clock logic device communicatively coupled to the detector array, a low-clock logic device communicatively coupled to the high-clock logic device, an accelerometer communicatively coupled to the low-clock logic device, and a processor communicatively coupled to the high-clock logic device. The low-clock logic device is configured to receive an acceleration signal from the accelerometer, determine that the acceleration signal corresponds to a wake gesture, and, in response to the determining, send a first power state change signal to the processor and a second power state change signal to the high-clock logic device, and cause the detector array to exit a stand-by state and enter a ready state in which image acquisition can be performed.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
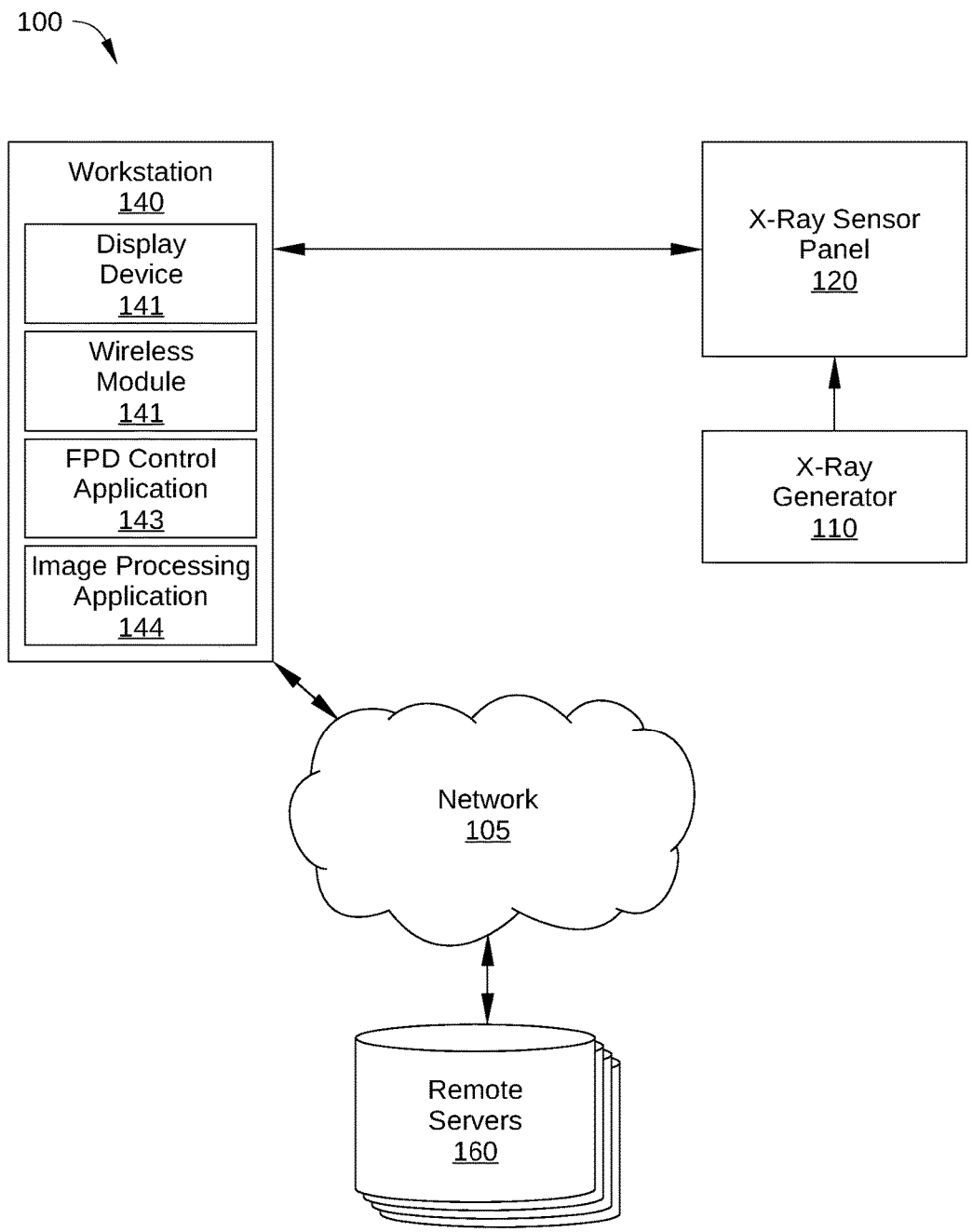
FIG. 1 is a block diagram of a digital radiographic X-ray acquisition system, according to one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

In light of the issues set forth in the background, there is a need in the art for a battery-powered X-ray sensor that addresses the above limitations of conventional X-ray sensors. According to embodiments of the present disclosure, a flat panel detector for a digital radiographic X-ray acquisition system is configured with a sleep or suspend function that reduces power consumption of certain components of the flat panel detector when idle, and a gesture-activated wake function that enables these components. In some embodiments, the wake gesture is a specific number of physical taps on an external surface of the X-ray panel sensor by the user, and the taps are detected by a low-power sensor that remains on in the sleep state, such as an accelerometer. Thus, the flat panel detector can be quickly brought out of the sleep state by a user while holding the flat panel detector. Consequently, delays and interruptions that result from maintaining the flat panel detector in a sleep state are minimized or otherwise reduced.

FIG. 1 is a block diagram of a digital radiographic X-ray acquisition system 100, according to one or more embodiments of the present disclosure. Digital radiographic X-ray acquisition system 100 is a digital radiography system that is configured to generate raw digital X-ray image data based on incident X-rays, and generate digital images based on the raw digital X-ray image data. As shown, digital radiographic X-ray acquisition system 100 includes an X-ray generator 110 and an X-ray sensor panel 120 that is wirelessly connected to a workstation 140, which in turn can connect to remote servers 160 via a network 105. In some embodiments, workstation 140 connects to remote servers 160 via a wireless access point (not shown). Alternatively or additionally, in some embodiments, X-ray sensor panel 120 is configured to wirelessly connect to remote servers 160 directly via network 105 and/or a wireless access point.

Network 105 may be any technically feasible type of communications network that allows data to be exchanged between digital radiographic X-ray acquisition system 100 and remote servers 160. Examples of network 105 may include a wide area network (WAN), a local area network (LAN), a wireless (WiFi) network, and/or the Internet, among others.

X-ray generator 110 can be any suitable X-ray source for emitting X-ray photons, such as an X-ray tube. Generally, X-ray generator 110 is controlled by workstation 140 or other computing device, via a wired or wireless connection. Specifically, workstation 140 enables selection of X-ray attributes suitable for a specific image acquisition or acquisition session. For example, workstation 140 can control the power supply of X-ray generator 110, thereby producing a desired peak kilovoltage (kVp), current, and duration of exposure.

Remote servers 160 are computing devices in which reside information pertinent to operation of X-ray sensor panel 120, such as user data, patient data, previously performed studies, and previously acquired images associated therewith. For example, in some embodiments, remote servers 160 include one or more Digital Image and Communications in Medicine (DICOM) servers, such as a DICOM picture archiving and communication system (PACS) storage server and/or a DICOM PACS review workstation. Such servers provide storage and convenient access to medical images from multiple modalities, thereby enabling a user of X-ray acquisition system 100 to immediately access previously generated medical images and/or studies associated with a particular patient or project.

Workstation 140 may be any technically feasible computing device that includes a display device 141, for displaying a user interface (UI) and is capable of wirelessly connecting to X-ray sensor panel 120, such as a (touch-sensitive or conventional) display screen. For example, in some embodiments, workstation 140 may be desktop or laptop computer that is configured to interact with (e.g., receive output from and provide input to) X-ray sensor panel 120. In other embodiments, workstation 140 may be a suitably programmed mobile computing device, such as a smartphone, a wearable computing device, or an electronic tablet. In either case, workstation 140 includes a wireless module 142 for enabling communication with X-ray sensor panel 120, and is programmed with one or more FPD control applications 143 that enable user interactions with X-ray sensor panel 120, such as configuring X-ray sensor panel 120, operating X-ray sensor panel 120, and performing FPD calibration procedures. In addition, in some embodiments, workstation 140 is programmed with an image processing application 144 for processing image data received from X-ray sensor panel 120. Image processing application 144 includes one or more applications for processing image data received from X-ray sensor panel 120 to generate a digital image. For example, in some embodiments, image processing application 144 may be configured to convert a digital representation or other image data into a digital image in a specific image file format and/or to modify the resultant digital image. Alternatively or additionally, in some embodiments, image processing application 144 may provide image processing capability for radiographic (still-picture X-ray) applications and/or fluoroscopic (video X-ray) applications. Alternatively or additionally, in some embodiments, image processing application 144 can include patient study editing software, image review and/or annotation software, image reprocessing software, and the like. Thus, once a digital representation is received from X-ray sensor panel 120, image generation and post-processing can be performed independently from the operation of X-ray sensor panel 120.

In some embodiments, workstation 140 may be further configured to query, over a network, a list of patients and studies to be performed, such as a DICOM Modality Worklist Server or other remote server 160; to locally store a list of patients and studies to be performed, similar to a DICOM Modality Worklist Server; to provide a user interface to access a locally stored patient/study list; to maintain a local record of studies performed and images acquired, such as a panel-resident version of a DICOM PACS; to provide a user interface to view and/or review such studies; and to transmit studies performed, including images, directly to one or more of remote servers 160.

X-ray sensor panel 120 is a battery-powered, wireless, radiographic flat panel detector that has a power state architecture that includes a sleep state for significantly reducing power consumption of X-ray sensor panel 120 when X-ray images are not being acquired. Specifically, upon entering the sleep state, certain components of X-ray sensor panel 120 are powered down, while other components of X-ray sensor panel 120 operate in a lower power state than when X-ray sensor panel 120 is in an active power state. In addition, X-ray sensor panel 120 includes a wake function that enables a user holding X-ray sensor panel 120 to cause X-ray sensor panel 120 to exit the sleep state via a wake gesture. By contrast, a user generally releases a conventional FPD from a sleep state by accessing a particular application on a workstation associated with X-ray sensor panel 120 and performing one or more input operations in the application. On embodiment of X-ray sensor panel 120 is illustrated in FIG. 2.

Figure 2:
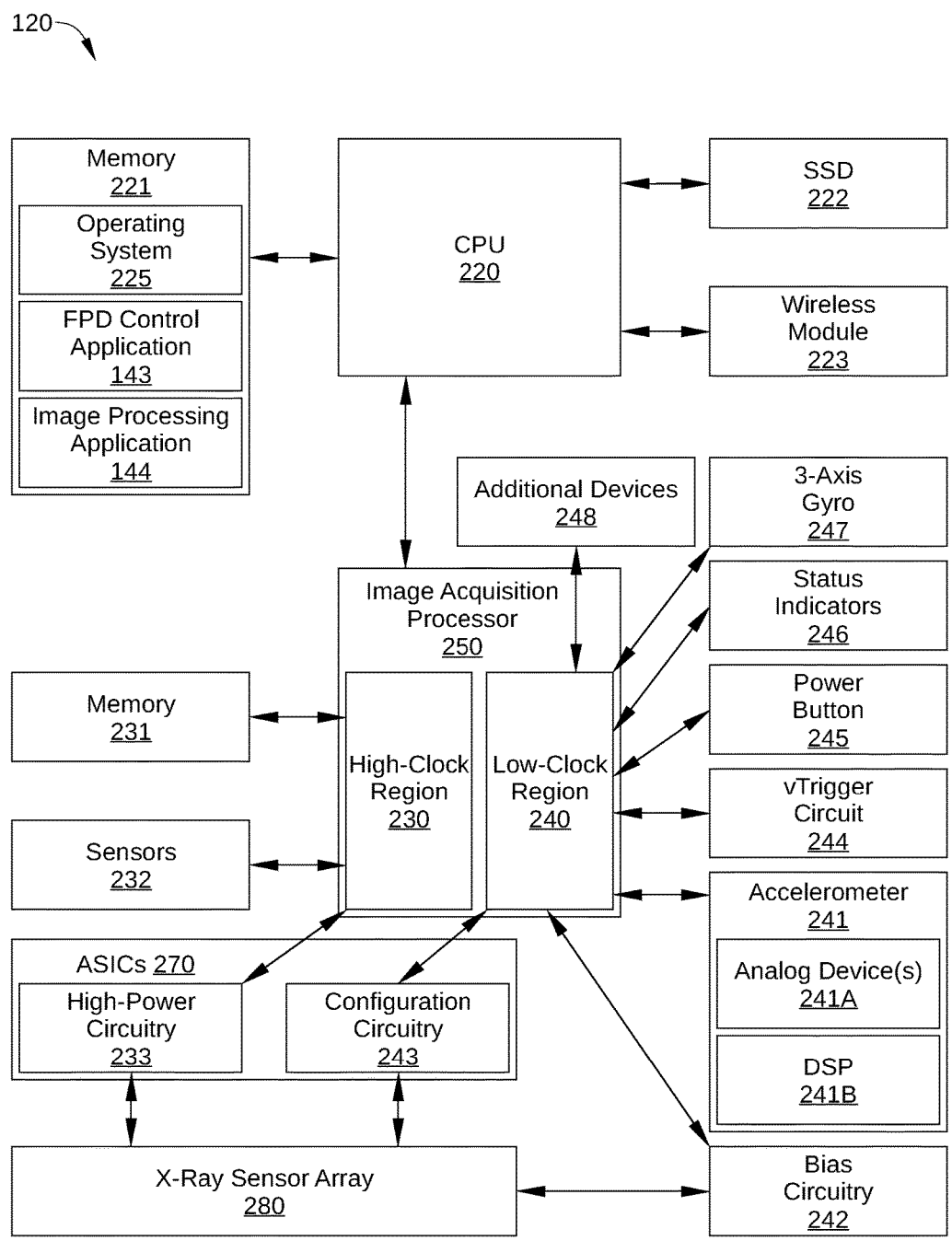
FIG. 2 schematically illustrates a hand-held detector of the digital radiographic X-ray acquisition system in FIG. 1, according to one or more embodiments of the present disclosure.

FIG. 2 is a block diagram of X-ray sensor panel 120, according to one or more embodiments of the present disclosure. As shown, X-ray sensor panel 120 includes a central processing unit (CPU) 220, an image acquisition processor 250 with a high-clock region 230 and a low-clock region 240, and a plurality of application-specific integrated circuits (ASICs) 270 coupled to an X-ray sensor array 280. CPU 220 is communicatively coupled to various devices, including one or more of a memory 221, a solid-state drive (SSD) 222 or other non-volatile data storage medium, and a wireless module 223. High-clock region 230 of image acquisition processor 250 is communicatively coupled to a memory 231, sensors 232, and high-power circuitry 233 of ASIC 270. Low-clock region 240 of image acquisition processor 250 is communicatively coupled to an accelerometer 241, bias circuitry 242, configuration circuitry 243 of ASIC 270, a voltage trigger (vTrigger) circuit 244, a power button 245, one or more status indicators 246, a three-axis gyro 247, and one or more additional devices 248.

CPU 220 may be any suitable processor implemented as a CPU, an application-specific integrated circuit (ASIC), a field programmable gate array (FPGA), any other type of processing unit, or a combination of different processing units. In some embodiments, CPU 220 is a Smart Mobility Architecture (SMARC) x86-based processor. In general, processing unit 220 may be any technically feasible hardware unit capable of processing data and/or executing software applications residing in memory 221, including an operating system (OS) 225, and, in some embodiments, FPD control application 143 and image processing application 144. CPU 220 is configured to read data from and write data to memory 221. Memory 221 may include a random access memory (RAM) module, a flash memory unit, any other type of memory unit, or a combination thereof. Memory 221 includes various software programs that can be executed by CPU 220 and application data associated with said software programs, including OS 225. In some embodiments, FPD control application 143 and/or image processing software 144 reside in memory 221. In the embodiment illustrated in FIG. 2, memory 221 is depicted as a separate device from CPU 220, but in other embodiments memory 221 can be included in CPU 220.

OS 222 supports the functions of CPU 220, including scheduling tasks and executing FPD control application 143 and/or image processing software 144, sending commands to SSD 222 and wireless module 223, and managing the power state of CPU 220.

SSD 222 provides non-volatile storage for previously acquired data or medical images, studies associated with a particular patient or project, and/or software applications. Wireless module 223 may be any technically feasible wireless chips, cards, or other devices that enable X-ray sensor panel 120 to communicate wirelessly with workstation 140 in FIG. 1 and/or with network 105 in FIG. 1. Examples of devices suitable for use as wireless module 223 include a WiFi module, a WLAN module, a 3G module, and the like. For example, in some embodiments, wireless module 223 is a 802.11ac/n device capable of providing a WiFi Direct connection to workstation 140. Alternatively or additionally, in some embodiments, wireless module 223 is a device capable of providing a Bluetooth connection to workstation 140. Thus, in some embodiments, wireless module 223 includes two antennas and is capable of both WiFi and Bluetooth operation simultaneously.

In some embodiments, image acquisition processor 250 is a separate processor from CPU 220 that controls and otherwise interacts with the image acquisition hardware of X-ray sensor panel 120. As such, image acquisition processor 250 may be any suitable processor implemented as a CPU, an ASIC, an FPGA, any other type of processing unit, or a combination of different processing units. In general, image acquisition processor 250 may be any technically feasible hardware unit capable of controlling the image acquisition hardware of X-ray sensor panel 120, receiving signals from the readout electronics of X-ray sensor array 280, generating a digital representation of an x-ray image based on the received signals, and transmitting the digital representation to CPU 220 for image processing. In other embodiments (not shown), image acquisition processor 250 is integrated with CPU 220.

In some embodiments, image acquisition processor 250 is an FPGA that includes high-clock region 230 and low-clock region 240. In such embodiments, the functionality of image acquisition processor 250 as described herein is implemented as image acquisition firmware that resides in high-clock region 230, low-clock region 240, or a combination of both. High-clock region 230 is a high-clock-rate logic device that performs time-dependent and/or computationally intensive actions, such as receiving signals from ASICs 270 during image acquisition, storing image-acquisition data in memory 231, processing image-acquisition data, etc. Low-clock region 240 is a low-clock-rate logic device that performs less computationally intensive and/or less time-sensitive operations, such as changing the current configuration of ASICs 270 via configuration circuitry 243 and controlling and/or processing signals from accelerometer 241, vTrigger circuit 244, power button 245, status indicators 246, 3-axis gyro 247, and/or other devices 248. In some embodiments, high-clock region 230 and low-clock region 240 are different portions of a single integrated circuit (IC) chip. In other embodiments, high-clock region 230 and low-clock region 240 are each implemented as separate IC logic chips.

Low-clock region 240 operates at a significantly lower clock rate and consumes significantly less power than high-clock region 230. For example, in one embodiment, low-clock region 240 operates at a clock-rate of about 24 MHz and consumes on the order of about 0.3 W while in typical operation, while high-clock region 230 operates at a clock-rate of about 200-400 MHz and consumes on the order of about 3-5 W while in typical operation, such as during image acquisition. Thus, low-clock region 240 can remain powered during a sleep or an idle mode without significantly reducing the useful battery life of X-ray sensor panel 120. It is noted that high-clock region 230 generally performs functions of image acquisition processor 250 that are only used in an active state and are not employed while X-ray sensor panel 120 is in a sleep state, such as image acquisition functions. Thus, high-clock region 230, and the functions of X-ray sensor panel 120 performed thereby, can be powered down while X-ray sensor panel 120 is in a sleep state without affecting the functionality of X-ray sensor panel 120.

Accelerometer 241 may be any technically feasible accelerometer configured to detect acceleration of X-ray sensor panel 120 and to generate and transmit a corresponding acceleration signal to image-acquisition processor 250. In some embodiments, accelerometer 241 is configured to detect acceleration of X-ray sensor panel 120 along one axis. Alternatively or additionally, accelerometer 241 is configured to detect acceleration of X-ray sensor panel 120 along two and/or three axes. In some embodiments, accelerometer 241 includes one or more analog devices 241A that generate an analog signal indicating a measured acceleration of X-ray sensor panel 120 along one or more axes, such as a micro-electromechanical systems (MEMS) accelerometer. In other embodiments, accelerometer 241 includes one or more additional devices (not shown) that generate a digital signal indicating a measured acceleration of X-ray sensor panel 120 along one or more axes. Thus the acceleration signal generated by accelerometer 241 can be an analog or digital signal.

In some embodiments, accelerometer 241 further includes a digital signal processor (DSP) 241B or other processor configured to perform one or more filtering functions on the acceleration signal generated by analog device(s) 241A. Thus, in such embodiments, the acceleration signal generated by accelerometer 241 can be a filtered signal. Such filtering functions can modify the acceleration signal so that accelerations resulting from a wake gesture can be more readily distinguished by suitable logic located in DSP 241B or in low-clock region 240.

According to various embodiments, a wake gesture performed by a user includes a specific number of physical taps on an external surface of X-ray sensor panel 120 by the user. For example, in such embodiments, the wake gesture may be a double-tap that occurs within a specified time interval, e.g., one second. Alternatively or additionally, in some embodiments, the wake gesture includes physically tapping a surface of the X-ray sensor panel 120 against an external object, such as a wall or floor, for a specific number of times within a specified time interval, e.g., one second. Alternatively or additionally, in some embodiments, the wake gesture includes shaking X-ray sensor panel 120 for a specified time interval. It is noted that other causes of acceleration of X-ray sensor panel 120 generally have a different rise time, magnitude, harmonic profile, and/or other detectable characteristics than a tap-based wake gesture, and therefore can be eliminated or reduced from an acceleration signal by the filtering functions performed by DSP 241B. For example, accidentally bumping X-ray sensor panel 120 against an object, dropping X-ray sensor panel 120, or transporting X-ray sensor panel 120 in a motor vehicle can all cause significant accelerations of X-ray sensor panel 120. However, filtering function included in DSP 241B can reduce the likelihood that such accelerations are erroneously determined to indicate a user-initiated wake gesture. Thus, when DSP 241B performs these filtering functions, detection of the accelerations typical of a user performing a wake gesture is greatly facilitated.

In some embodiments, DSP 241B may also be configured with logic to determine whether accelerations measured by analog device(s) 241A indicate that a user has performed a wake gesture, such as when X-ray sensor panel 120 is tapped against an object by a user, or when a user manually taps a surface of X-ray sensor panel 120. In such embodiments, the acceleration signal transmitted to low-clock region 240 by accelerometer 241 is an indicator signal that notifies low-clock region 240 that a wake gesture has been identified. Alternatively, in other embodiments, such logic is included in low-clock region 240. In such embodiments, the acceleration signal from accelerometer 241 may be an analog or digital signal indicating accelerations experienced by X-ray sensor panel 120.

Bias circuitry 242 is configured to apply a small negative voltage, for example approximately −1 V, to the light-detecting diodes of X-ray sensor array 280 when X-ray sensor panel 120 is in a sleep mode. With this low voltage applied thereto, the light-detecting photodiodes of X-ray sensor array 280 can be quickly brought to an active state in which image acquisition can be performed in response to incident X-ray photons. In addition, bias circuitry 242 is configured to apply a higher negative bias to the photodiodes of X-ray sensor array 280 (for example −3 to −5 V) to increase the response time and signal output of the photodiodes. Biasing the photodiodes in this way increases the signal output by modifying the conditions experienced by the diodes when incident X-ray photons are received.

VTrigger circuit 244 is configured to detect incident X-rays on X-ray sensor array 280 when the photodiodes of X-ray sensor array 280 are in a low-power, ready state, i.e., when bias circuitry 242 applies a voltage to the photodiodes of X-ray sensor array 280. In addition, vTrigger circuit 244 is configured to send a notification to low-clock region 240 that incident X-rays have been detected. Low-clock region 240 then triggers image acquisition by causing the photodiodes of X-ray sensor array 280 to enter an active state via bias circuitry 242 and configuration circuitry 243.

Power button 245 enables various user inputs to control the power state of CPU 220, image acquisition processor 250, and/or X-ray sensor panel 120 as a whole. For example, in some embodiments, when X-ray sensor panel 120 is off, pressing power button 245 for more than a certain time interval, such as one second, results in image acquisition processor 250 turning on and booting up. In some embodiments, when X-ray sensor panel 120 is operating in an active state, pressing power button 245 for a longer time interval, for example between one and three seconds, results in X-ray sensor panel 120 exiting any lower power state, such as an idle state or a sleep state, and entering a normal operating power state. In some embodiments, when X-ray sensor panel 120 is operating in an active state, pressing power button 245 for a still longer time interval, for example between three and six seconds, results in X-ray sensor panel 120 attempting to shut down. In some embodiments, when X-ray sensor panel 120 is operating in an active state, pressing power button 245 for an even longer time interval, for example greater than six seconds, results in CPU 220 and image acquisition processor 250 immediately shutting down. In other embodiments, any other technically feasible user input scheme may be employed in conjunction with power button 245 to cause FDP 120 to enter a certain power state.

Status indicators 246 include visual indicators, such as one or more color-coded light-emitting diodes (LEDs) and/or audible indicators, such as one or more buzzers or speakers. Status indicators 246 can provide information to a user associated with one or more of current power state, battery state, wireless communication state, system state, completion of a current image acquisition, and the like.

3-axis gyro 261 indicates the precise orientation of X-ray sensor panel 120 during X-ray image acquisition, even when there is motion of X-ray sensor panel 120 at that time. Thus, metadata indicating up/down/left/right for a particular image can be collected at the time of image acquisition. In some embodiments, accelerometer 241 can also indicate when X-ray sensor panel 120 has been bumped, thereby preventing signals generated by X-ray sensor array 280 during such a bump from being interpreted as an image signal generated in response to incident X-rays.

Other devices may also be included in X-ray sensor panel 120 and communicatively coupled to low-clock region 240, including one or more digital-to-analog converts (DACs) and/or analog-to-digital converters (ADCs), a power monitor, a shock sensor, a battery or supercapacitor, temperature sensors, and the like.

ASICs 270 include the readout electronics and analog devices for measuring voltage generated by the amorphous silicon photodiodes of X-ray sensor array 280. For example, in some embodiments, ASICs 270 include analog ASIC devices that each generate a voltage that is proportional to incident visible light on a particular pixel region of X-ray sensor array 280. As shown, ASICs 270 include high-power circuitry 233 and configuration circuitry 243. High-power circuitry 233 is energized during image acquisition to read out charge generated by the photodiodes of X-ray sensor array 280. Configuration circuitry 243 connects each ASIC in ASICs 270 with image acquisition processor 250 to enable changing the power state and otherwise controlling each ASIC in ASICs 270. For example, in some embodiments, configuration circuitry 243 includes a configuration bus. High-power circuitry 233 is energized during image acquisition, but is not powered when X-ray sensor panel 120 is in a ready state, i.e., ready to receive incident X-rays, or when X-ray sensor panel 120 is in a sleep state. By contrast, configuration circuitry 243 is generally energized when X-ray sensor panel 120 is in the ready state or in a sleep state.

X-ray sensor array 280 includes a glass plate with a matrix or array of pixel detector elements formed thereon that each convert incident X-ray photons to electrical charge. In embodiments in which X-ray sensor panel 120 is configured as an indirect flat panel detector, a scintillator material in X-ray sensor panel 120 is excited by incident X-rays and emits light, which is detected by a plurality of photodiodes. Each photodiode generates a signal (e.g., a voltage that is proportional to incident light intensity) for a different pixel of what will eventually become a digital image. An encoder (which may be, for example, included in high-clock region 230) then interprets each of these voltages and assigns a value to each that is proportional to the voltage. One such embodiment of X-ray sensor array 280 is illustrated in FIG. 3.

Figure 3:
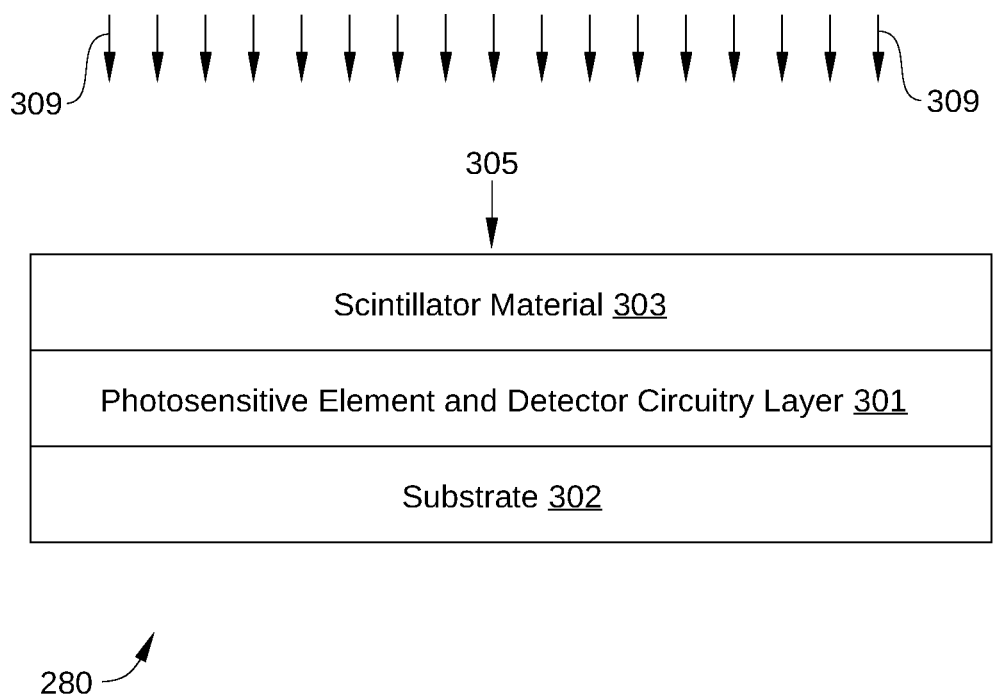
FIG. 3 schematically illustrates a cross-sectional view of an X-ray sensor panel of the X-ray detector of FIG. 2, according to one embodiment of the disclosure.

FIG. 3 schematically illustrates a cross-sectional view of X-ray sensor array 280, according to one embodiment of the disclosure. As shown, X-ray sensor array 280 includes a photosensitive element and detector circuitry layer 301 formed on a substrate 302 and a layer of scintillator material 303 formed on photosensitive element and detector circuitry layer 301. Also shown are incident X-rays 309 that have passed through a patient, sample, or other object of interest after being generated by X-ray generator 110. Together, photosensitive element and detector circuitry layer 301, substrate 302, and scintillator material 303 form an X-ray imaging matrix 305. It is noted that photosensitive element and detector circuitry layer 301 is generally formed from a plurality of processing layers, and that X-ray imaging matrix 305 may include additional material layers not illustrated in FIG. 3.

Photosensitive element and detector circuitry layer 301 generally includes a plurality of photosensitive elements, such as photodiodes, photogates, phototransistors, or any other suitable circuitry suitable for operation as pixel detector elements in X-ray sensor array 280. For example, photosensitive element and detector circuitry layer 301 may also include thin-film transistors (TFTs) for reading out the digital signals from the pixel detector elements. Scintillator material 303 may include one or more material layers including, but not limited to, gadolinium oxisulfide ($Gd_2O_2S$:Tb), cadmium tungstate ($CdWO_4$), bismuth germanate ($Bi_4Ge_3O_{12}$ or BGO), cesium iodide (CsI), or cesium iodide thallium (CsI:Tl)), among others.

In the embodiment illustrated in FIG. 3, X-ray sensor array 280 is depicted as an indirect flat panel detector, in which X-ray photons are converted to other light photons that are in turn detected and converted into charge. In other embodiments, X-ray sensor array 280 can be a direct flat panel detector. In a direct FPD, incident X-ray photons are converted directly into charge in an amorphous selenium layer, and the resultant charge pattern therein is read out by suitable hardware, such as a thin-film transistor (TFT) array, an active matrix array, microplasma line addressing, or the like.

Figure 4:
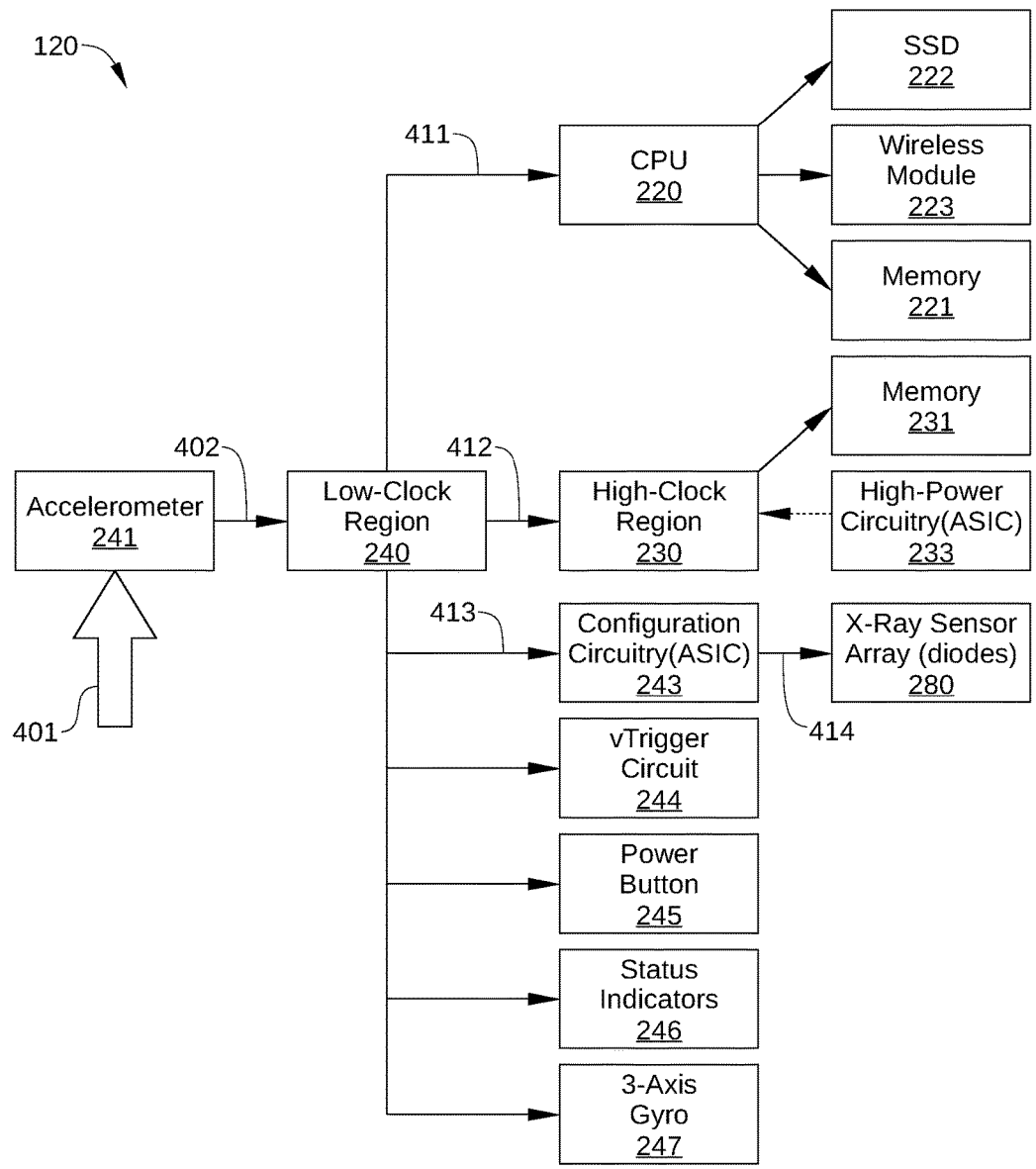
FIG. 4 is an operational block diagram of the flat-panel detector of FIG. 2, according to one or more embodiments of the present disclosure.

FIG. 4 is an operational block diagram of X-ray sensor panel 120 waking from a sleep state in response to a wake gesture, according to one or more embodiments of the present disclosure. The sleep state is a power conserving state in which some or most components of X-ray sensor panel 120 are not powered. The sleep state can be substantially equivalent to the S3 sleep state in embodiments in which X-ray sensor panel 120 is a Windows-based system, the sleep mode or hibernate mode 0 in embodiments in which X-ray sensor panel 120 is a MacOS-based system, or the suspend mode in embodiments in which X-ray sensor panel 120 is a Linux-based system. Such a power state is referred to generically herein as a "sleep state".

As shown, when accelerometer 241 receives a wake gesture 401 while in a sleep state, accelerometer 241 sends an acceleration signal 402 to low-clock region 240. Low-clock region 240 determines, based on acceleration signal 402, that a wake gesture has been performed by a user on X-ray sensor panel 120, and transmits a first power state change signal 411 to CPU 220, such as a Peripheral Component Interconnect Express (PCIe) wake signal, and a second power state change signal 412 to high-clock region 230. In addition, low-clock region 240 causes the photodiodes of X-ray array 280 to exit a stand-by state and enter a ready state in which image acquisition can be performed. For example, in some embodiments, low-clock region 240 transmits a ready panel signal 413 to configuration circuitry 243. Configuration circuitry 243 then biases the photodiodes of X-ray array 280 with a higher negative voltage 414 than when in the stand-by state, thereby making X-ray sensor array 280 ready to generate image data when X-ray photons are incident thereon. In some embodiments, in response to determining that a wake gesture has been performed by the user on X-ray sensor panel 120, low-clock region 240 also transmits one or more additional power state change signals, such as activation signals, as shown, to one or more of vTrigger circuitry 243, power button 245, status indicators 246, and three-axis gyro 247.

In response to receiving first power state change signal 411, CPU 220 enters a higher power state than the sleep state, and activates one or more of memory 221, SSD 222, and wireless module 223. For example, in embodiments in which CPU 220 receives the first power state change signal 411 while in an S3 sleep state, in response CPU 220 enters a higher power consumption state than the S3 sleep state, such as a low-power-but-active power consumption state (e.g., an S0 low awake state in a Windows-based system), or a high active state (e.g., an S0 high active state in a Windows-based system). In such embodiments, in the lowpower-but-active power consumption state, CPU 220 is awake and ready to receive image data and/or to perform image data processing, whereas in the high active state, CPU 220 operates in a standard operating state, and is generally receiving image data from high-clock region 230 and/or processing such image data.

In response to receiving second power state change signal 412, high-clock region 230 changes from a lower-power state, such as an un-powered state, to a higher power state, such as a ready state or an active state. For example, in some embodiments, in the ready state, high-clock region 230 is ready to receive signals from high-power circuitry 233 of ASICs 270 in response to incident X-rays striking X-ray sensor array 280. In addition, in the active state, high-clock region 230 is receiving and processing such signals from ASICs 270.

Figure 5:
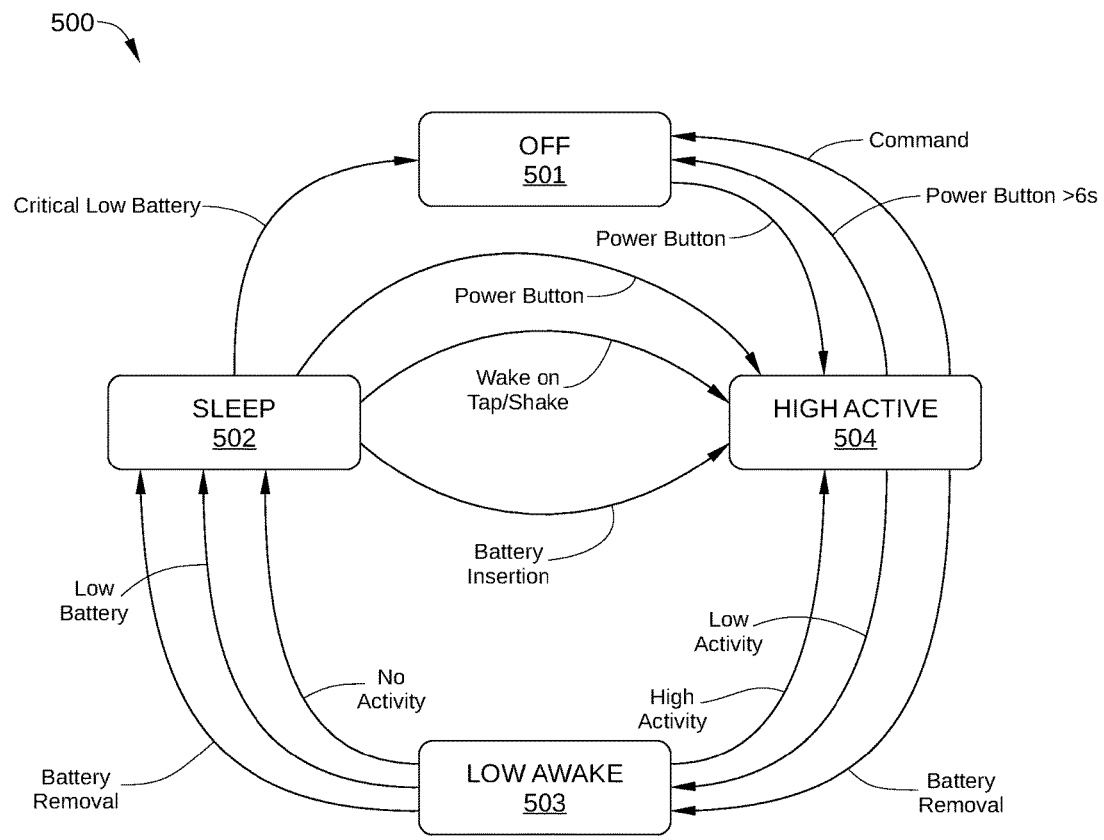
FIG. 5 is a power state diagram for the flat-panel detector of FIG. 2, according to various embodiments of the present disclosure.

FIG. 5 is a power state diagram 500 for X-ray sensor panel 120, according to various embodiments of the present disclosure. As shown, X-ray sensor panel 120 operates in four different power states: an off state 501, a sleep state 502, a low awake state 503, and a high active state 504.

In sleep state 502, no software is operating in CPU 220, memory 221 is in a refresh mode, and SSD 222 and wireless module 223 are powered down. In addition, high-clock region 230 of image acquisition processor 250 is powered down, as well as memory 231, other sensors 232, and high-power circuitry 233 of ASICs 270. By contrast, 502, low-clock region 240, configuration circuitry 243, and bias circuitry 242 are powered on in sleep state 502. In addition, the photodiodes of X-ray sensor array 280 have a low negative bias applied thereto (for example −1 V), and can be quickly made ready to receive light generated by X-ray photons incident on X-ray sensor array 280.

In some embodiments, sleep state 502 is substantially similar to an S1, S2, or S3 sleep state for CPU 220. In such embodiments, X-ray sensor panel 120 enters high active state 504 when power button 245 is depressed for a particular duration of time (for example, one to three seconds), when a battery insertion event is detected (for example by low-clock region 240), or when a wake gesture is detected by low-clock region 240. In some embodiments, when a wake gesture is detected by low-clock region 240, low-clock region 240 employs a PCIe wake mechanism to cause CPU 220 to enter high active state 504 from sleep state 502. X-ray sensor panel 120 enters sleep state 502 from low awake state 503 in response to low battery detection, detection of a battery removal event, or no activity for more than a maximum time threshold, for example 30 seconds. X-ray sensor panel 120 enters off state 501 from sleep state 502 when a critical battery power is detected.

In low awake state 503, CPU 220 operates in a low-power-but-active power consumption state. For example, for Windows-based systems low awake state 503 may be substantially similar to an S0 low awake state or a Deepest Runtime Idle Platform State (DRIPS). Thus, low awake state 503 is a lower power consumption state than a normal operating state, such as high active state 504, but CPU 220 is awake and ready to receive image data and/or to perform image data processing. As such, operating system 225 executes on CPU 220, but power consumption by operating system 225 is minimized or otherwise reduced relative to when CPU 220 is in high active state 504. In some embodiments, one or more cores included in CPU 220 may be parked or otherwise powered down in low awake state 503. In some embodiments, SSD 222 and wireless module 223 are also powered on in low awake state 503. In addition, in low awake state 503, high-clock region 230, low-clock region 240, memory 231, and vTrigger circuit 244 are powered on and active. Further, the photodiodes of X-ray sensor array 280 have a negative bias applied thereto (for example −3 to −5 V) and are ready to receive light generated by X-ray photons incident on X-ray sensor array 280. In some embodiments, one or more additional components of X-ray sensor panel 120 are also powered on in low awake state 503, including power button 245, one or more status indicators 245, 3-axis gyro 247, and additional devices 248. Alternatively, in some embodiments, one or more of the above-described additional component of X-ray sensor panel 120 are not powered on in low awake state 503, and are instead only powered on in high active state 504.

X-ray sensor panel 120 enters low awake state 503 from high active state 504 in response to low activity detection. Low activity detection can be performed by CPU 220 or by image acquisition processor 250, and can occur when: no user inputs are received for a time interval exceeding a predetermined threshold; the activity level of CPU 220 is such that one or more cores of CPU 220 can be parked or otherwise powered down; and/or image acquisition processor 250 completes transmission of image data to CPU 220. In some embodiments, X-ray sensor panel 120 also enters low awake state 503 upon detection of a battery removal event. X-ray sensor panel 120 exits low awake state 503 and enters high active state 504 when high activity is detected. Such high activity detection can be performed by CPU 220 or by image acquisition processor 250, and can occur when: user inputs are received via wireless module 223 from workstation 140; image acquisition processor 250 begins transmission of image data to CPU 220; and/or the activity level of CPU 220 is such that one or more cores of CPU 220 need to be powered up or otherwise activated, such as when image data are being received from image acquisition processor 250, documents or image data are being received or transmitted via wireless module 223, image processing is being performed with CPU 220, etc.

In high active state 504, CPU 220 operates in a standard operating state, such as an S0 high active state. Thus, high active state 504 is a higher power consumption state than low awake state 503, and CPU 220 is awake and receiving image data and/or performing image data processing. In addition, in high active state 504, high-clock region 230, low-clock region 240, memory 231, high-power circuitry 233, and vTrigger circuit 244 are powered on and active. Further, the photodiodes of X-ray sensor array 280 have a larger negative bias applied thereto (for example −3 to −5 V) and are ready to receive light generated by X-ray photons incident on X-ray sensor array 280, and/or are receiving such light.

X-ray sensor panel 120 enters high active state 504 from off state 501 in response to power button 245 being depressed, and from low awake state 503 in response to detecting a high activity level, as described above. X-ray sensor panel 120 enters off state 501 from high active state 504 in response to power button 245 being depressed for an extended time interval, such as greater than six seconds, or in response to a software command, for example via a user input to workstation 140. According to various embodiments, X-ray sensor panel 120 enters high active state 504 from sleep state 502 in response to determining that a wake gesture is performed by a user. Specifically, X-ray sensor panel 120 enters high active state 504 from sleep state 502 when low-clock region 240 receives an acceleration signal from accelerometer 241 and determines that the acceleration signal corresponds to a wake gesture. In some embodiments, X-ray sensor panel 120 also enters high active state 504 from sleep state 502 in response to power button 245 being depressed.

As illustrated by power state diagram 500, X-ray sensor panel 120 is configured to minimize or otherwise reduce power consumption when in sleep state 502, and to quickly enter high active state 504 based on a wake gesture. Specifically, by reducing power consumption of CPU 220 and powering off non-essential components of X-ray sensor panel 120 in sleep state 502, battery life of X-ray sensor panel 120 is extended. It is noted that for a typical processor, power consumption in high active state 504 may be on the order of about 20 W, power consumption in low awake state 503 may be on the order of about 5 W, and power consumption in sleep state 502 may be on the order of about 0.5 W. In addition, by powering components of X-ray sensor panel 120 in sleep state 502 that enable detection of a wake gesture that is performed by a user, X-ray sensor panel 120 can be quickly and conveniently brought to high active state 504. Thus, a user can wake X-ray sensor panel 120 without using inputs via workstation 140

Figure 6:
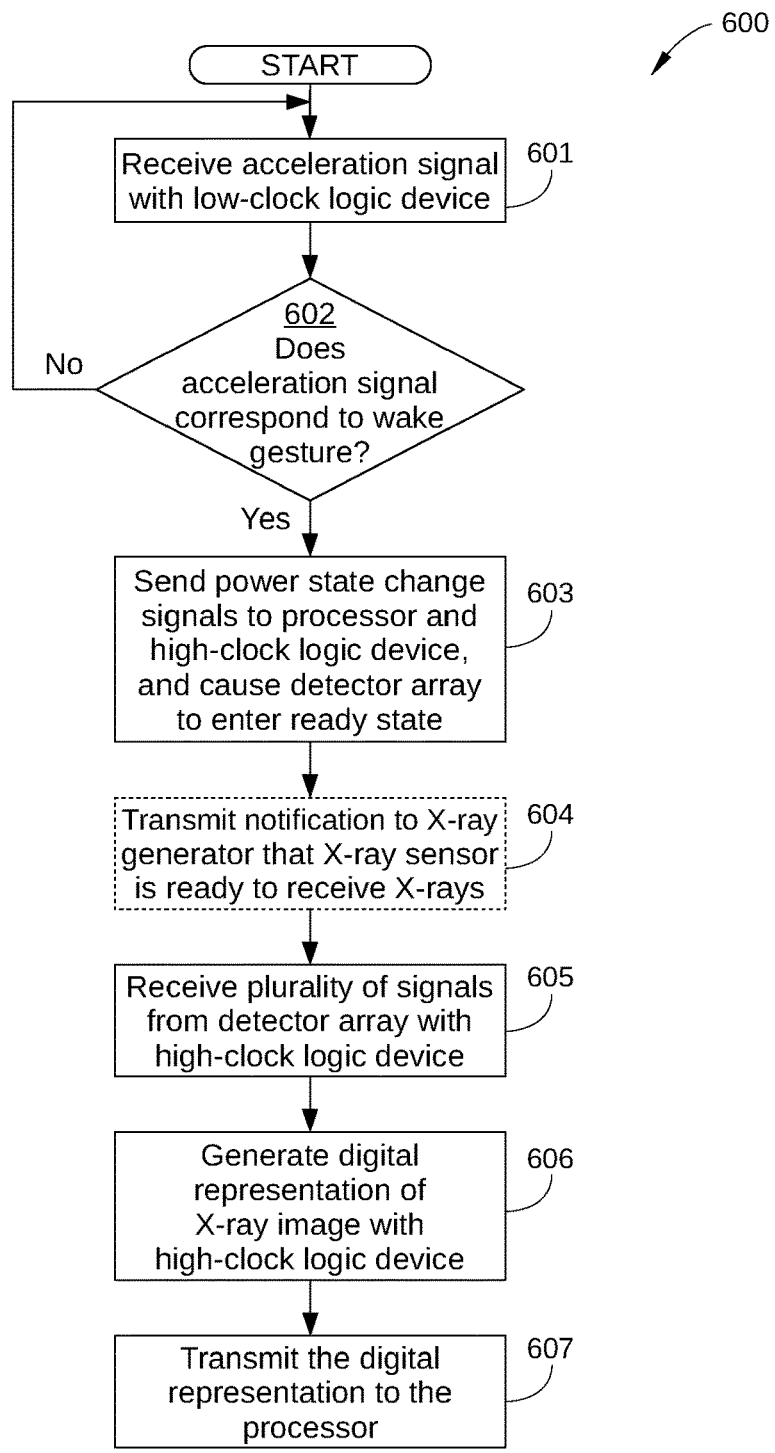
FIG. 6 sets forth a flowchart summarizing an example method for waking a flat-panel detector from a sleep state, according to one or more embodiments of the present disclosure.

FIG. 6 sets forth a flowchart summarizing an example method for waking a flat-panel detector from a sleep state, according to one or more embodiments of the present disclosure. The method may include one or more operations, functions, or actions as illustrated by one or more of blocks 601-607. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with digital radiographic X-ray acquisition system 100 of FIGS. 1-5, persons skilled in the art will understand that any suitably configured radiographic system is within the scope of the invention.

Prior to the method step, X-ray sensor panel 120 enters sleep state 502. In some embodiments, X-ray sensor panel 120 enters sleep state 502 in response to a user entering a sleep command via workstation 140 to X-ray sensor panel 120 while X-ray sensor panel 120 is in low awake state 503. In some embodiments, X-ray sensor panel 120 enters sleep state 502 in response to detecting that no activity has occurred for a time interval that exceeds a predetermined duration, for example 30 seconds. In such embodiments, no activity is considered detected when no image data from x-ray sensor array 280 is received by image acquisition processor 250 and no image data processing (including sending and receiving image data) is performed by CPU 220. It is noted that accelerometer 241 and low-clock region 240 are both activated in sleep state 502.

A method 600 begins at step 601, in which low-clock region 240 receives an acceleration signal from accelerometer 241.

In step 602, low-clock region 240 determines whether the acceleration signal received in step 601 corresponds to a wake gesture being performed by a user on X-ray sensor panel 120. If no, method 600 proceeds back to the start and low-clock region 240 continues to listen for an acceleration signal; if yes, method 600 proceeds to step 603. As noted above, a wake gesture can include a specified number of taps (for example, two), within a specified time interval (for example, one second) on a surface of X-ray sensor panel 120. Alternatively or additionally, a wake gesture can include tapping of X-ray sensor panel 120 against an object for a specified number of times within a specified time interval. Alternatively or additionally, a wake gesture can include shaking X-ray sensor panel 120 for a minimum number of back-and-forth iterations or for a time interval greater than a minimum time duration.

In step 603, low-clock region 240 sends a first power state change signal to CPU 220 and a second power state change signal to high-clock region 230, and causes the photodiodes of X-ray array 280 to exit a stand-by state and enter a ready state in which image acquisition can be performed. In the ready state, a higher negative bias is applied to the photodiodes of X-ray sensor array 280 than in the stand-by state.

In optional step 604, X-ray sensor panel 120 transmits a notification to X-ray generator 110 via wireless module 223 that X-ray sensor panel 120 is ready to receive X-rays.

In step 605, high-clock region 230 receives a plurality of signals from ASICs 270 in response to X-ray photons incident on X-ray sensor array 280.

In step 606, high-clock region 230 generates a digital representation of an X-ray image. For example, the digital representation may include an intensity value for each pixel of X-ray sensor array 280, as well as suitable metadata associated with the intensity values. In some embodiments, some or all of the digital representation is temporarily stored in memory 231 until transmitted to CPU 220.

In step 607, high-clock region 230 transmits the digital representation of the X-ray image to CPU 220 for subsequent data processing or transmission to workstation 140.

In sum, a flat panel detector for a digital radiographic X-ray acquisition system is configured with a sleep function that reduces power consumption of certain components of the flat panel detector when idle, and a gesture-activated wake function that enables these components. In some embodiments, the wake gesture includes a specific number of physical taps on an external surface of the X-ray panel sensor by the user, which can be detected by a low-power sensor that remains on in the sleep state, such as an accelerometer. Thus, the flat panel detector can be quickly brought out of the sleep state by a user while holding the flat panel detector. Consequently, delays and interruptions that result from maintaining the flat panel detector in a sleep state are minimized or otherwise reduced.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

We claim:

1. A computer-implemented method for changing a power state in a hand-held X-ray sensing apparatus including a processor, an accelerometer, a high-clock logic device, a low-clock logic device, and a detector array, the method comprising:
   receiving an acceleration signal from the accelerometer;
   determining with the low-clock logic device that the acceleration signal corresponds to a wake gesture; and
   in response to determining that the acceleration signal corresponds to the wake gesture, sending, from the low-clock logic device, a first power state change signal to the processor and a second power state change signal to the high-clock logic device.

2. The computer-implemented method of claim 1, wherein the first power state change signal comprises a wake signal that causes the processor to change from a lower-power sleep state to a higher-power active state.

3. The computer-implemented method of claim 2, wherein, in the higher-power active state, the processor activates at least one of a non-volatile memory associated with the processor and included in the hand-held X-ray sensor, and a wireless communication module associated with the processor and included in the hand-held X-ray sensor.

4. The computer-implemented method of claim 2, wherein, in the higher-power active state, the processor executes an application configured to receive image data from the high-clock logic device.

5. The computer-implemented method of claim 1, further comprising, in response to determining that the acceleration signal corresponds to the wake gesture, causing the detector array to exit a stand-by state and enter a ready state in which image acquisition can be performed.

6. The computer-implemented method of claim 1, wherein the second power state change signal causes the high-clock logic device to change from a power off state to a power on state.

7. The computer-implemented method of claim 6, further comprising, in response to the high-clock logic device receiving a plurality of signals from the detector array while the high-clock logic device is in the power on state:
  generating, with the high-clock logic device, a digital representation of an X-ray image based on the plurality of signals; and
  transmitting the digital representation from the high-clock logic device to the processor while the processor is in a higher-power active state.

8. The computer-implemented method of claim 7, further comprising, in response to receiving the digital representation from the high-clock logic device, generating with the processor a digital image based on the digital representation.

9. The computer-implemented method of claim 1, wherein causing the detector array to exit the stand-by state and enter the ready state comprises causing charge reading elements in the detector array to enter a high-power state in which electric charge generated by incident X-rays can be measured.

10. An X-ray sensing apparatus, comprising:
  a detector array configured to generate a plurality of signals in response to x-rays incident on the detector array during an exposure period;
  a high-clock logic device communicatively coupled to the detector array;
  a low-clock logic device communicatively coupled to the high-clock logic device;
  an accelerometer communicatively coupled to the low-clock logic device; and
  a processor communicatively coupled to the high-clock logic device,
  wherein the low-clock logic device is configured to:
  receive an acceleration signal from the accelerometer;
  determine that the acceleration signal corresponds to wake gesture; and
  in response to determining that the acceleration signal corresponds to the wake gesture, send a first power state change signal to the processor and a second power state change signal to the high-clock logic device.

11. The X-ray sensing apparatus of claim 10, wherein the first power state change signal comprises a wake signal that causes the processor to change from a lower-power sleep state to a higher-power active state.

12. The X-ray sensing apparatus of claim 11, wherein, in the higher-power active state, the processor activates at least one of a non-volatile memory associated with the processor and included in the hand-held X-ray sensor, and a wireless communication module associated with the processor and included in the hand-held X-ray sensor.

13. The X-ray sensing apparatus of claim 11, wherein, in the higher-power active state, the processor executes an application configured to receive image data from the high-clock logic device.

14. The X-ray sensing apparatus of claim 10, wherein the processor is further configured to cause the detector array to exit a stand-by state and enter a ready state in which image acquisition can be performed.

15. The X-ray sensing apparatus of claim 10, wherein the second power state change signal causes the high-clock logic device to change from a power off state to a power on state.

16. The X-ray sensing apparatus of claim 15, wherein the high-clock logic device is configured to, in response to receiving a plurality of signals from the detector array while in the power on state:
  generate a digital representation of an X-ray image based on the plurality of signals; and
  transmit the digital representation to the processor while the processor is in a higher-power active state.

17. The X-ray sensing apparatus of claim 10, wherein the low-clock logic device and the high-clock logic device are included in a single integrated circuit chip.

18. The X-ray sensing apparatus of claim 10, wherein the acceleration signal comprises a notification from a processor included in the accelerometer that the acceleration signal corresponds to a wake gesture, and determining with the low-clock logic device that the acceleration signal corresponds to the wake gesture comprises receiving the notification.

19. The X-ray sensing apparatus of claim 10, wherein the acceleration signal comprises an analog or digital output from the accelerometer that is generated when the wake gesture is performed by a user, and determining with the low-clock logic device that the acceleration signal corresponds to the wake gesture comprises performing an algorithm with the low-clock logic device.

20. An X-ray sensing apparatus, comprising:
  a processing means;
  an image acquisition means, communicatively coupled to the processing means and a detector array, wherein
    the detector array is configured to generate a plurality of signals in response to x-rays incident on the detector array during an exposure period, and
    the image acquisition means is configured to generate a digital representation of an X-ray image based on the plurality of signals that is communicatively coupled to the detector array; and
  an accelerometer communicatively coupled to the image acquisition means, wherein the image acquisition means is further configured to:
  receive an acceleration signal from the accelerometer;
  determine that the acceleration signal corresponds to a wake gesture; and
  in response to determining that the acceleration signal corresponds to the wake gesture, send a first power state change signal to the processing means and a second power state change signal to the image acquisition means.

* * * * *